(12) United States Patent
Rasekhi

(10) Patent No.: US 10,258,201 B1
(45) Date of Patent: Apr. 16, 2019

(54) APPARATUS FOR MILLING MATERIAL

(71) Applicant: Houshang Rasekhi, Sandy, UT (US)

(72) Inventor: Houshang Rasekhi, Sandy, UT (US)

( * ) Notice: Subject to any disclaimer, the term of this patent is extended or adjusted under 35 U.S.C. 154(b) by 774 days.

(21) Appl. No.: 14/859,188

(22) Filed: Sep. 18, 2015

Related U.S. Application Data

(60) Provisional application No. 62/071,305, filed on Sep. 19, 2014.

(51) Int. Cl.
| | |
|---|---|
| *A47J 43/00* | (2006.01) |
| *A47J 43/25* | (2006.01) |
| *A61F 2/46* | (2006.01) |
| *B02C 19/20* | (2006.01) |

(52) U.S. Cl.
CPC .......... *A47J 43/255* (2013.01); *A61F 2/4644* (2013.01); *B02C 19/20* (2013.01); *A61F 2002/4645* (2013.01)

(58) Field of Classification Search
CPC ............................... A47J 43/255; B02C 19/20
USPC .......................................... 241/92, 262, 280
See application file for complete search history.

(56) References Cited

U.S. PATENT DOCUMENTS

| | | | | |
|---|---|---|---|---|
| 2,271,175 A * | 1/1942 | Mantelet | ........... | A47J 43/255 241/280 |
| 2,695,643 A * | 11/1954 | Aberer | ........... | A47J 43/255 241/273.3 |
| 3,032,087 A * | 5/1962 | Rodwick | ........... | A47J 43/255 241/245 |
| 3,810,555 A * | 5/1974 | Bakker | ........... | B27L 11/002 144/176 |
| 3,985,304 A * | 10/1976 | Sontheimer | ........... | A47J 43/0777 241/92 |
| 4,002,298 A * | 1/1977 | Latora | ........... | A47J 43/255 241/278.1 |
| 4,226,370 A * | 10/1980 | Watson | ........... | B02C 4/12 241/207 |
| 4,610,398 A * | 9/1986 | Palazzolo | ........... | B26D 1/29 241/278.1 |
| 4,655,403 A * | 4/1987 | Sciortino | ........... | F25C 5/12 241/278.1 |
| 4,856,718 A * | 8/1989 | Gaber | ........... | A47J 43/07 241/93 |
| 5,364,037 A * | 11/1994 | Bigelow | ........... | A47J 43/255 241/169.1 |
| 5,445,332 A * | 8/1995 | Shimizu | ........... | A47J 43/082 241/100 |

(Continued)

*Primary Examiner* — Faye Francis
(74) *Attorney, Agent, or Firm* — Michael Dodd; Dodd Law Group

(57) ABSTRACT

Rasp systems for controlled milling of cortical, cancellous or combinations disclosed. The disclosed rasp system may provide morselized bone with predetermined particle-size distribution for automatic milling apparatus. The rasp systems comprises a rasp for cutting material and a push surface to effect directing and sweep the material over surface of the rasp for controlled milling material disclosed. The bone-cutting tooth having side cutters disclosed. In addition, radial rasp systems with self-generating centrifugal forces for pushing material against the rasp surface for automatic milling apparatus disclosed. Furthermore, embodiments can include a battery-powered autoclaveable milling apparatuses for automatic milling cortical, cancellous or combinations of bone material utilizing said radial rasp systems disclosed.

10 Claims, 15 Drawing Sheets

(56) References Cited

U.S. PATENT DOCUMENTS

| | | | | |
|---|---|---|---|---|
| 5,660,341 | A * | 8/1997 | Perkins | A47J 43/255 241/169.1 |
| 5,803,378 | A * | 9/1998 | Wolters | A47J 43/255 241/100 |
| 5,983,769 | A * | 11/1999 | Schneider | A47J 43/255 241/101.4 |
| 6,244,529 | B1 * | 6/2001 | Tardif | A47J 43/255 241/100 |
| 7,137,581 | B2 * | 11/2006 | Takayama | A47J 43/255 241/169.1 |
| 7,337,997 | B2 * | 3/2008 | Ko | A47J 43/255 241/168 |
| 7,588,202 | B2 * | 9/2009 | Rasekhi | A61F 2/4644 241/100 |
| 8,196,850 | B2 * | 6/2012 | Rasekhi | A61F 2/4644 241/100 |
| 2003/0173435 | A1 * | 9/2003 | Hernandez | A47J 43/0722 241/92 |
| 2014/0014751 | A1 * | 1/2014 | Sampaio | A47J 43/255 241/93 |

* cited by examiner

APPARATUS FOR MILLING MATERIAL

RELATED APPLICATION

This application claims the benefit of and priority to U.S. Provisional Patent Application Ser. No. 62/071,305, entitled "Improved Apparatus For Milling Material, filed Sep. 19, 2014 by Houshang Rasekhi, the entire contents of which are expressly incorporated by reference.

TECHNICAL FIELD

The present invention relates generally to milling methods and devices. More specifically, the present invention relates to apparatus for milling material, particularly milling bone.

BACKGROUND

The autogenic bones harvested from the bones of the same person during the same operating procedures or allogenic (living tissue transferred between two genetically different individuals of the same species), cut into smaller pieces to create morselized bone for grafting procedures in repair or augmenting skeletons.

The harvested bone may include combined cortical and cancellous bone that referred to as corticocancellous bone. The bone structure of the cancellous bone may be of the honeycomb construct containing the bone marrow. The weight bearing cortical bone is the dense and hard outer layer of the bone. In grafting, the implanted bone becomes the scaffold that needed for new bone formation. Therefore, the bone milling process must preserve the bone tissue structures and properties as much as possible.

The corticocancellous bone harvested from a spine may include larger amount of cortical bone (mostly cortical); while the bone harvested from a femoral head may include larger amount of cancellous bone (mostly cancellous).

The available bone mills generally suffer from inability to morselize of both mostly-cortical or mostly-cancellous bone; and preserving the bone tissue structure properties.

The available manually operated bone mills require excessive manual milling force and may suffer from inability to produce an adequate amount of morselized corticocancellous bone (e.g., 20 to 100 cc) within the operating room time constraints. Considering the cost per minute associated with surgical operating rooms, and the supporting staff, the manually operated bone mills may lose their price advantage; and indeed may effectively be significantly expensive, instead.

Furthermore, the available powered bone mills suffer from inability to mill the corticocancellous bone, transferring heat to the milled bone particles that may cause bone necrosis, or producing cortical thin bone shavings that may not be suitable for bone grafting.

For example, in the case of bone mill functioning similar to a coffee grinder, the milled bone remain in the milling chamber until the end of the milling process. During milling, milled particles unnecessarily undergo severe impacts with each other, with the walls of the mill, and with the dull fast rotating blade, mashing the bone structure of the cancellous bone particles and perhaps imparting heat energy that may damage the milled particles. Further, bone mill of coffee grinder design often fail to complete the needed milling. It may create very fine milled cancellous bone, "the mush" and some dust-like milled cortical bone particles, and not-milled pebble-like remaining cortical bone pieces that are beyond the mill's ability to mill. Therefore, these types of powered bone mills suffer from inability to provide the proper bone particle-size distribution profile needed for proper bone grafting.

For another example, the powered bone mill functioning as a saw-crusher often produces large bone slivers that may not be suitable for utilization in bone graft. These types of bone mills may suffer from inability to provide morselized bone with a predetermined particle-size distribution.

In some other cases, such as when the bone mill functions as a powered grater, the short-height of the cutting teeth of the blade create bone shavings which may not be suitable for proper bone grafting. Increasing the height of the cutting teeth for producing thicker strips of cortical bone requires cutting forces beyond the ability of a bone mill suitable in size for operating room environment. These types of bone mills may often suffer from inability to provide morselized corticocancellous bone with the desired particle size distribution profile and properties. Further, a portion of the harvested milled bone, trapped in the plastic blade shroud, become waste. Thus, inherently this type bone mills suffer because of low yield.

Other available bone mills utilize a cut-and-trim method of milling bone These bone mills are equipped with cortical cutting blade that is capable of cutting and sizing cortical or mostly cortical bone but fails to efficiently mill cancellous bone.

Focusing on the material cutting process, the design of a conventional cutting tooth is for cutting and removing a small amount of material per tooth throughout the cutting path. Such cutting tooth comprises a cutting edge, a primary positively angled relief surface and an angled rake. The combination of the positively angled relief surface and positively angled rake surface may create forces pulling the cutting tooth into the material for continual cutting throughout the cutting path.

Utilizing the full height of a conventional cutting tooth in cutting bone may result in grating instead of morselizing bone into small particle sizes. As such, the tooth may wedge into the bone, which may require substantial cutting force to continue cutting.

Not having the needed capable bone mill for milling cortical, cancellous, and corticocancellous bone in the operating room environment, often operating room personnel manually cut harvested bone into small pieces for grafting. Hand cutting bone is time consuming and could increase probability of infecting the graft.

Accordingly, in most, if not all, cases, conventional bone mills fail to successfully produce adequate amount of morselized bone with the needed particle-size distribution profile. (e.g., see N. T. Brewster, Mechanical consideration in impaction bone grafting. THE JOUNAL OF BONE AND JOINT SURGERY. Vol. 81-B, No. 1. January 1999).

SUMMARY OF THE INVENTION

Aspects of the invention are directed to rasp systems for milling material, particularly milling cortical, cancellous, or corticocancellous bone for bone grafting, including an improved bone-cutting tooth for nibbling bone into appropriately sized particles. One aspect is more particularly directed to rasp systems capable of providing properly morselized cancellous or corticocancellous bone with proper particle-size distribution profile, which may have superior biomechanics, when impacted.

A bone cutting rasp can include a negative relief angle, angled face with angled side-cutting edges, and an aperture disposed adjacent the inclined face disclosed. A bone-milling apparatus can include bone-cutting teeth, and push forces to effect morselization of bone that may have predictable particle sizes disclosed.

In one aspect, a radial bone milling apparatus includes a hollow radial rasp, a push surface having a resilient member, and a power-driving module for morselization of bone disclosed.

A radial bone-cutting rasp can provide morselized bone with predetermined particle-size distribution for automatic milling. In addition, an automated bone-milling apparatus with self-generating centrifugal forces can include the radial rasp; a rotor having a cavity for containing bone chips and a push surface for sweeping the bone chips over the radial rasp; a catch container for collecting the milled particulates; a safety cap; and a battery-powered module for driving the rotor disclosed.

Accordingly, aspects include a milling apparatus capable of consistently providing the needed morselized corticocancellous, cancellous, or cortical bone without substantially damaging the bone tissue structures and properties; and with the needed proper particle-size distribution profile.

BRIEF DESCRIPTION OF THE DRAWINGS

Exemplary embodiments of the invention will become more fully apparent from the following description and appended claims, taken in conjunction with the accompanying drawings. With the understanding that these drawings depict only exemplary embodiments and are, therefore, not to be considered limiting of the invention's scope, the exemplary embodiments of the invention will be described with additional specificity and detail through use of the accompanying drawings in which:

DETAILED DESCRIPTION

Various embodiments of the invention now described with reference to the Figures, where like reference numbers indicate identical or functionally similar elements. The embodiments of the present invention, as generally described and illustrated in the Figures herein, could be arrange and designed in a wide variety of different configurations. Thus, the following more detailed description of several exemplary embodiments of the present invention, as represented in the Figures, is not intended to limit the scope of the invention, as claimed, but is merely representative of the embodiments of the invention.

The word "exemplary" is used exclusively herein to mean "serving as an example, instance, or illustration." Any embodiment described herein as "exemplary" is not necessarily should construe as preferred or advantageous over other embodiments.

As used herein, the terms "an embodiment," "embodiment," "embodiments," "the embodiment," "the embodiments," "one or more embodiments," "some embodiments," "certain embodiments," "one embodiment," "another embodiment" and the like mean "one or more (but not necessarily all) embodiments of the disclosed invention(s)," unless expressly specified otherwise.

The phrase "based on" does not mean", "based only on," unless expressly specified otherwise. In other words, the phrase "based on" describes both "based only on" and "based at least on."

Figure 1:
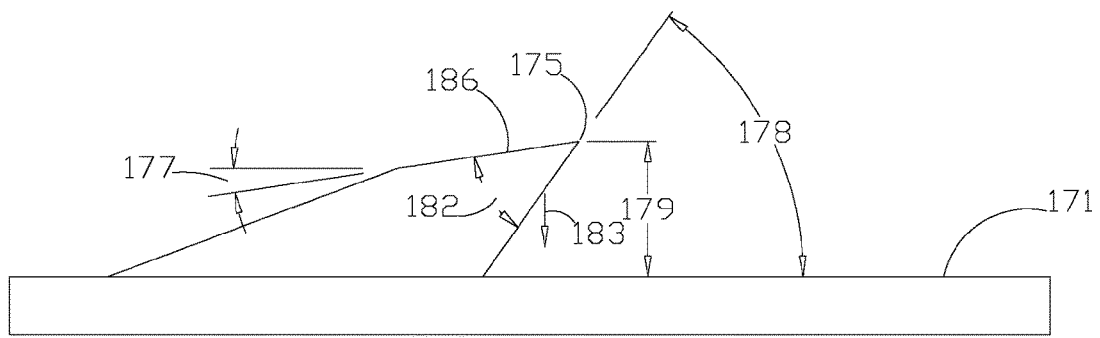
FIG. 1 is a perspective view of a conventional cutting tooth.

FIG. 1 is a perspective view of an embodiment of a conventional cutting tooth comprising a cutting edge 175 with cutting angle 182, relief surface 186 with positive angle 177 and angled rake surface with angle 178 rising from surface 171 for cutting material to the height 179. During continuous cutting the angled rake surface may cause force 183 pulling material down into the tooth that may maintain continuous-cutting throughout the cutting path. Utilizing the full height 179 of such a tooth in cutting bone may prevent controlling the length of the cut. Further, it could wedge into the material, i.e. bone, which may require substantial cutting force to continue cutting, often resulting in jams, wasting bone and time.

Figure 2:
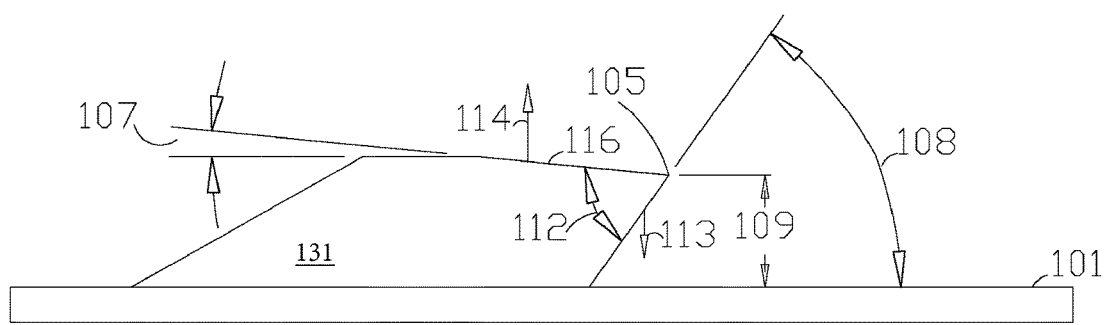
FIG. 2 is a perspective view of a cutting tooth with negative relief angle for milling bone.

FIG. 2 is a perspective view of an embodiment of a cutting tooth 131 raised from surface 101 for cutting material. Cutting tooth 131 comprises: a cutting edge 105 with cutting angle 112, a negatively angled relief surface 116 with angle 107, and an angled rake surface with angle 108 for cutting bone morsels of height 109.

Utilizing the full height 109 of a single tooth for cutting bone, the rake surface may cause force 113 pulling material down into the tooth and the negative angle 107 of the relief surface 116 may cause an opposing force 114 pushing the material out of the cutting path. Thus, the negative angle 107 may cause limiting the length of the cut. Accordingly, changing the angle 107 from positive to negative value may changes the tooth from a continuous-cutting-tooth to a nibbling-tooth. Increasing the negative angle 107 may increase the force 114, which in turn reduces the length of the cut, which may create bone morsels.

For example, in practice and in a particular case, teeth similar to the tooth shown in FIG. 2 became nibbling teeth having a 5 degrees negative angle 107; that limited the cut length of the cortical morsels to approximately two to four times the height 109.

Increasing the cutting angle 112 may reduce the cutting efficiency, the bite, of the tooth.

Figure 3:
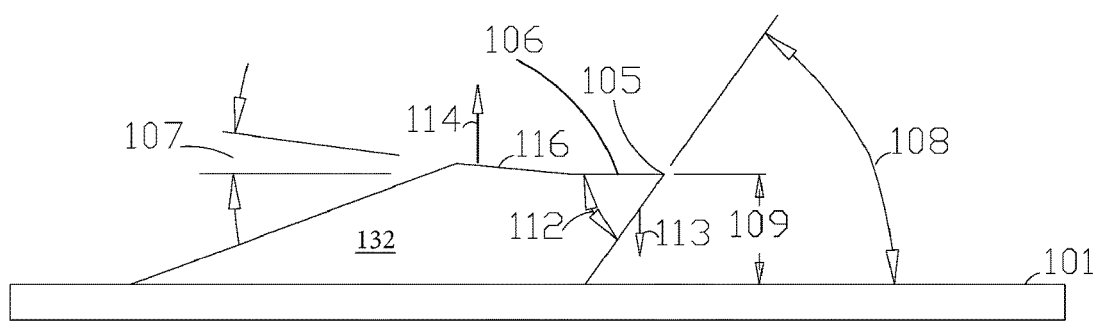
FIG. 3 is a perspective view of a cutting tooth with compounded negative relief angle for milling bone.

FIG. 3 is a perspective view of an embodiment of a cutting tooth 132 raised from surface 101. Cutting tooth 132 comprises: a cutting edge 105 with cutting angle 112, multiple relief surfaces 116 and 106, and rake angle 108. The surface 106 may have a positive angle respect to the surface 101, which may more efficiently penetrate either cancellous or cortical bone. The negatively angled relief surface 116 with the angle 107 may generate force 114 opposing force 113 pushing the material away from the cutting edge 105 that may promote nibbling action.

Figure 4:
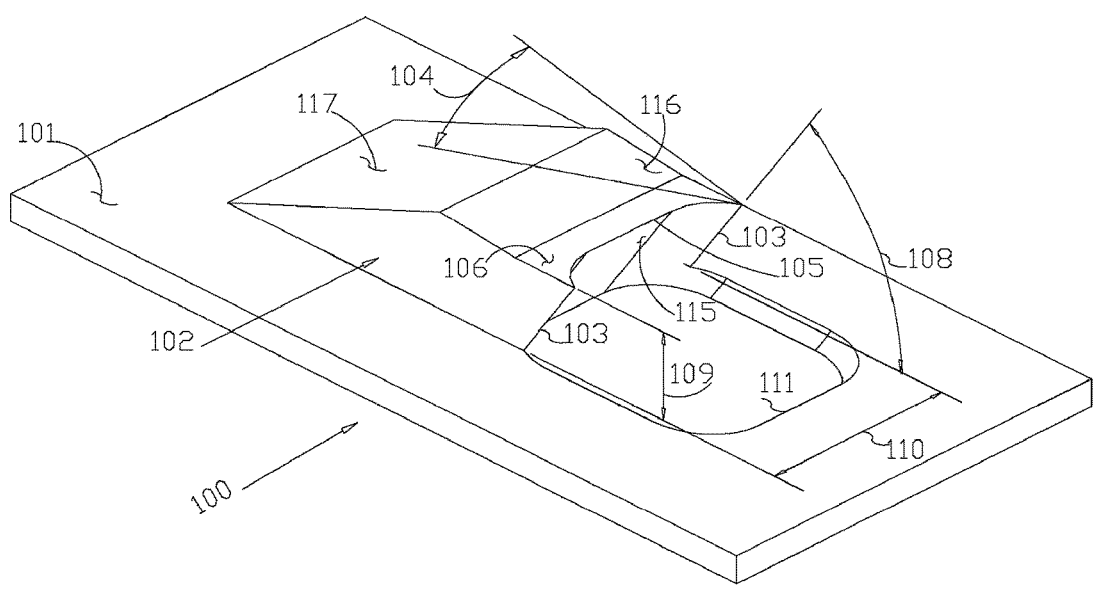
FIG. 4 is a perspective view of a rasp with compounded negative relief angle and angled side cutters for milling bone.

FIG. 4 is a perspective view of an embodiment of a rasp 100 that may cut corticocancellous bone or similar materials in predictable predictable-sizes. Rasp 100 comprises a cutting tooth 102 rising from the surface 101. Cutting tooth 102 comprises side-cutting edges 103 with inclined angle 108 and cutting angle 104, cutting edge 105, relief surface 106, relief surface 116, rake surface 115 and aperture 111. The angled edges 103 may cut morsels to the width 110. Thus, tooth 102 may cut material with morsels having approximately height 109, width 110 and length determined by the angle 107 (shown in FIGS. 2 and 3) and the size of the relief surface 116. As shown in FIG. 3 and FIG. 4 the relief surface 116 or a portion of the relief surface 116 may rise above the cutting edge 105 or height 109, with respect to the surface 101.

The aperture 111 may align with the inclined face 115 of the cutting tooth 102. For the purpose of this disclosure, align may include aligning a portion of the inclined face 115 with a portion of the aperture 111 that may facilitate the action of removing the milled material, from the milling zone, as will be explained further below.

For example, the aperture 111 and the inclined face 115 of the tooth 102 may formed by milling into the rasp 100. A milling tool may enter the rasp 100 at an angle that is not perpendicular to the base surface 101, such that an axis of the inclined face 115 and an axis of the aperture 111 may be at an angle from the base surface 101 of less than approximately ninety degrees. The width of the aperture may approximately equal to the width 110 or larger.

Figure 5:
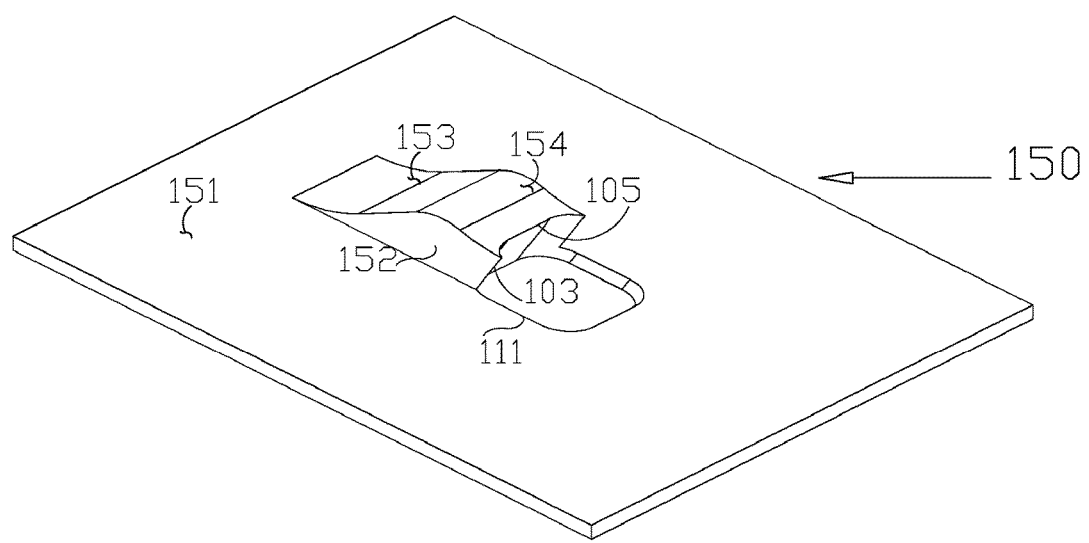
FIG. 5 is a perspective view of a rasp with compounded negative relief angle and angled side cutters produced in practice for milling bone.

FIG. 5 is a perspective view of an embodiment of rasp 150 for control cutting morsels of cortical bone, cancellous bone, or similar materials. Rasp 150 comprises a cutting tooth 152 rising from the surface 151. The surfaces 106, 116, and 117 shown in FIG. 4 may combine to create a smooth surface 153. As shown in FIG. 5, a portion 154 of the surface 153 rises above the cutting edge 105 with respect to the surface 151. Portion 153 may provide the nibbling process when cutting bone or similar material.

Figure 6:
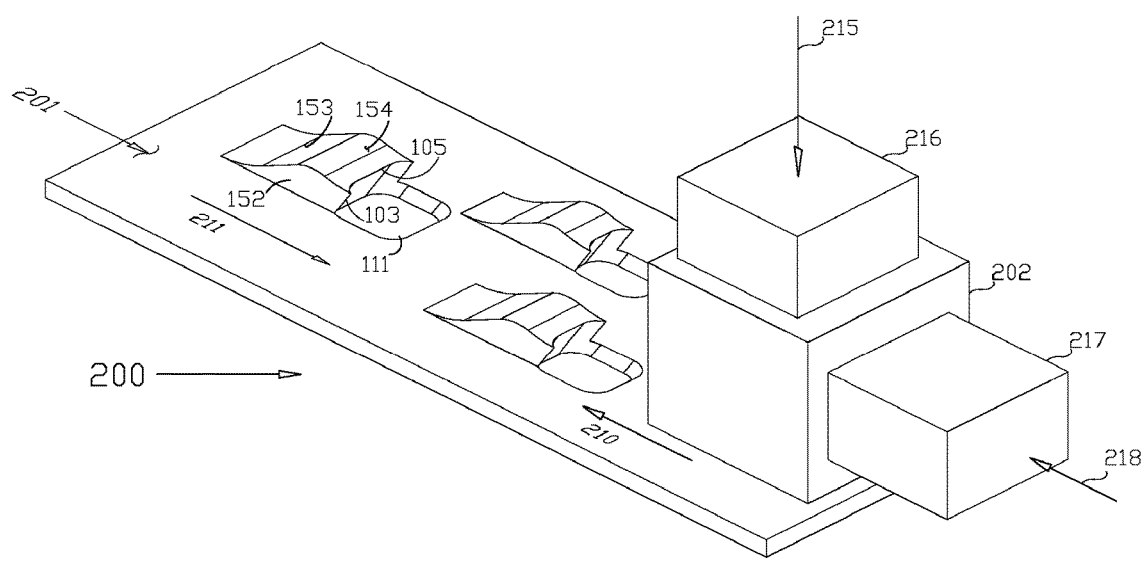
FIG. 6 is a perspective view of a milling apparatus with multiple teeth of different sizes for milling bone.

FIG. 6 is a perspective view of a basic milling apparatus 200 for milling bone. Basic milling apparatus 200 comprises: a rasp 201, a pusher 217, and a resilient member 216.

As depicted in FIG. 6, the rasp 201 includes three different sizes of bone-nibbling tooth, similar to the tooth 152, shown in FIG. 5. Apparatus 200 having different sizes of bone-nibbling teeth may provide morsels of different sizes for a predetermined particle size distribution profile.

The rasp 201 and the pusher 217 may move relative to each other in the directions 210 and 211. For example, the rasp 201 may move with respect to the pusher member 217. The pusher member 217 driven by the force 218 may move with respect to the rasp 201. The rasp 201 and the pusher member 217 may move with respect to each other. The rasp 201 and the pusher member 217 may move circularly, longitudinally, rotationally, or in any other direction that may allow the rasp 201 and the material 202 to interface for milling.

The force 215 may push the resilient member 216, which in turn pushes the material 202 on the surface of the rasp 201 for milling. The resilient member 216 may allow the material 202 freedom of movement for nibbling actions, as explained in conjunction with FIGS. 2, 3, and 4.

For example, as the material 202 engages the tooth 152 the cutting edge 105 and the angled side cutting edges 103 may begin penetrating the material 202 that may define and establish three shearing planes for cutting a morsel. The raised surface 154 may push the material 202 away from the cutting edge 105 that determines the length of the morsel as explained in conjunction with the FIGS. 2, 3, and 4.

The force 215 may be of the centrifugal type, which is a resilient force and may not need the resilient member 216. The force 215 may be of the manual type that may need the resilient member 216 for the milling apparatus to function properly. Further, the force 215 may be of the pneumatic type such as a sealed or pressurized pneumatic cylinder. The force 215 may be of any type including electrical or gravity forces.

Figure 7:
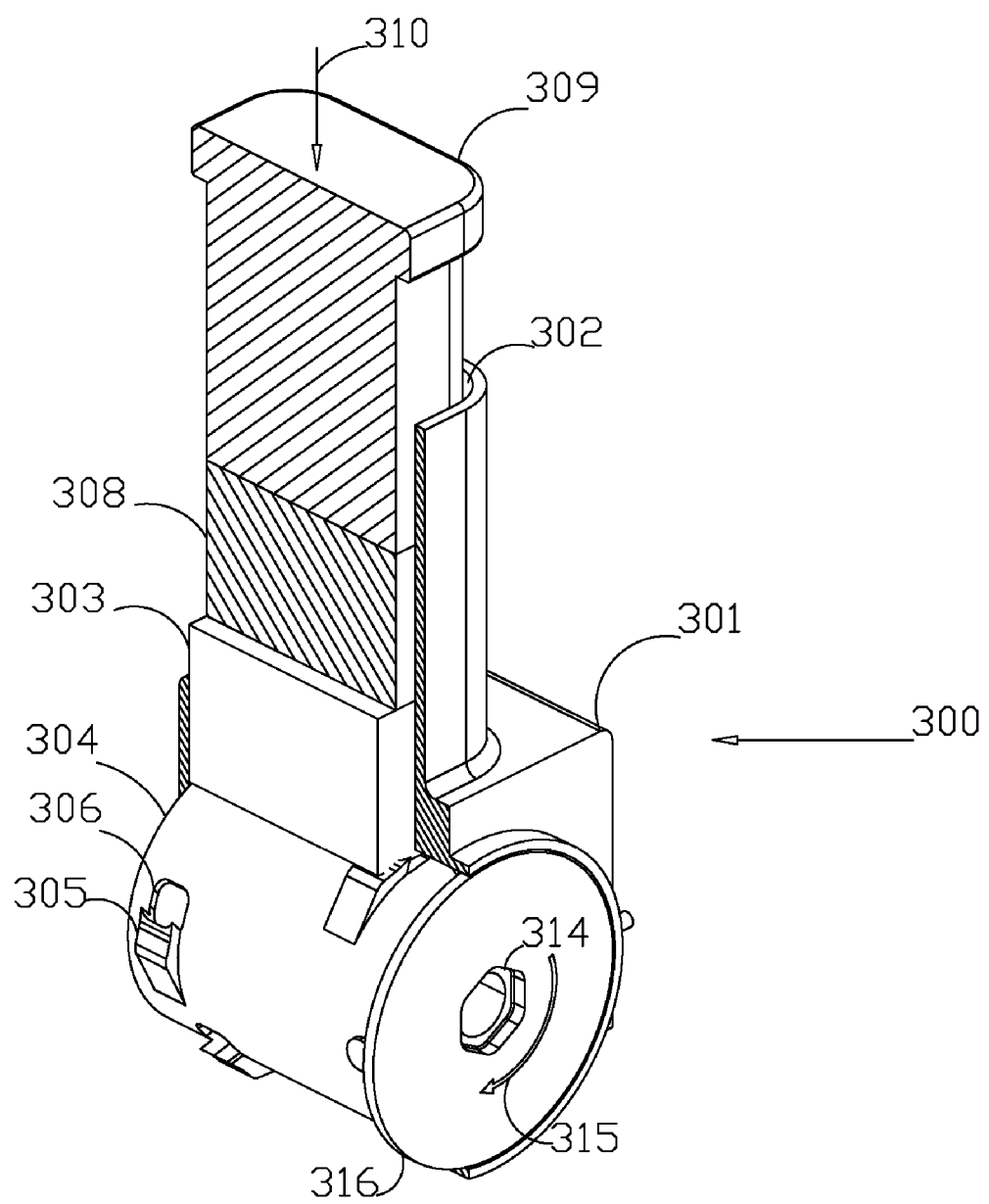
FIG. 7 is a perspective-sectioned view of a milling apparatus.

FIG. 7 is a perspective-sectioned view of a milling apparatus 300 for milling material 303. The apparatus 300 comprises: frame 301; pusher 309 with a resilient member 308; chute 302 for confining and guiding material 303 on to a hollow cylindrical rasp 304 with multiple cutting teeth 305 each having aperture 306; a removable lid 316, which includes a coupling 314 for rotationally driving the rasp 304.

For milling, rasp 304 may rotate in the direction 315 and force 310 may push the pusher 309, which in turn pushes the resilient member 308 against the material 303, which interfaces with the rasp 304. The rasp 304 rotating in the direction 315, with the nibbling-teeth 305 may engage and remove portions of the material 303. The removed portions, morsels, may eject through the aperture 306 into the hollow space of the cylindrical rasp 304, stored for future use.

To minimize the needed milling power, the teeth 305 are spaced from each other circumferentially and along the axial of rotation such that one tooth 305 engages material 303 at a time for milling.

Figure 8:
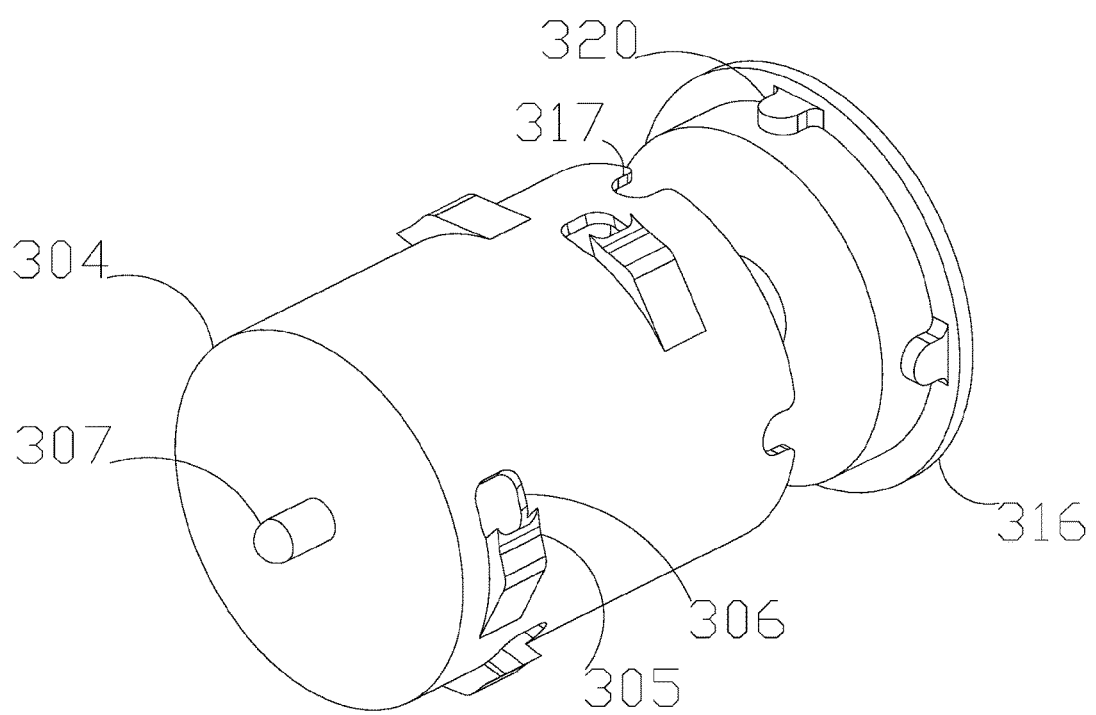
FIG. 8 is a perspective exploded view of the cylindrical rasp for milling bone from FIG. 7.

FIG. 8 is a perspective exploded view of the cylindrical rasp 304 showing the stabilizing pin 307, and coupling notches 317 for interfacing with the removable lid 316. The driving key 320 may interface with the notch 317 for rotating the cylindrical rasp 304 for milling.

The rasp 304 may receive the lid 316 to become an assembled unit. The stabilizing pin 307 may insert in a designated opening (e.g., shown in FIG. 11) located in the frame 301.

Figure 9:
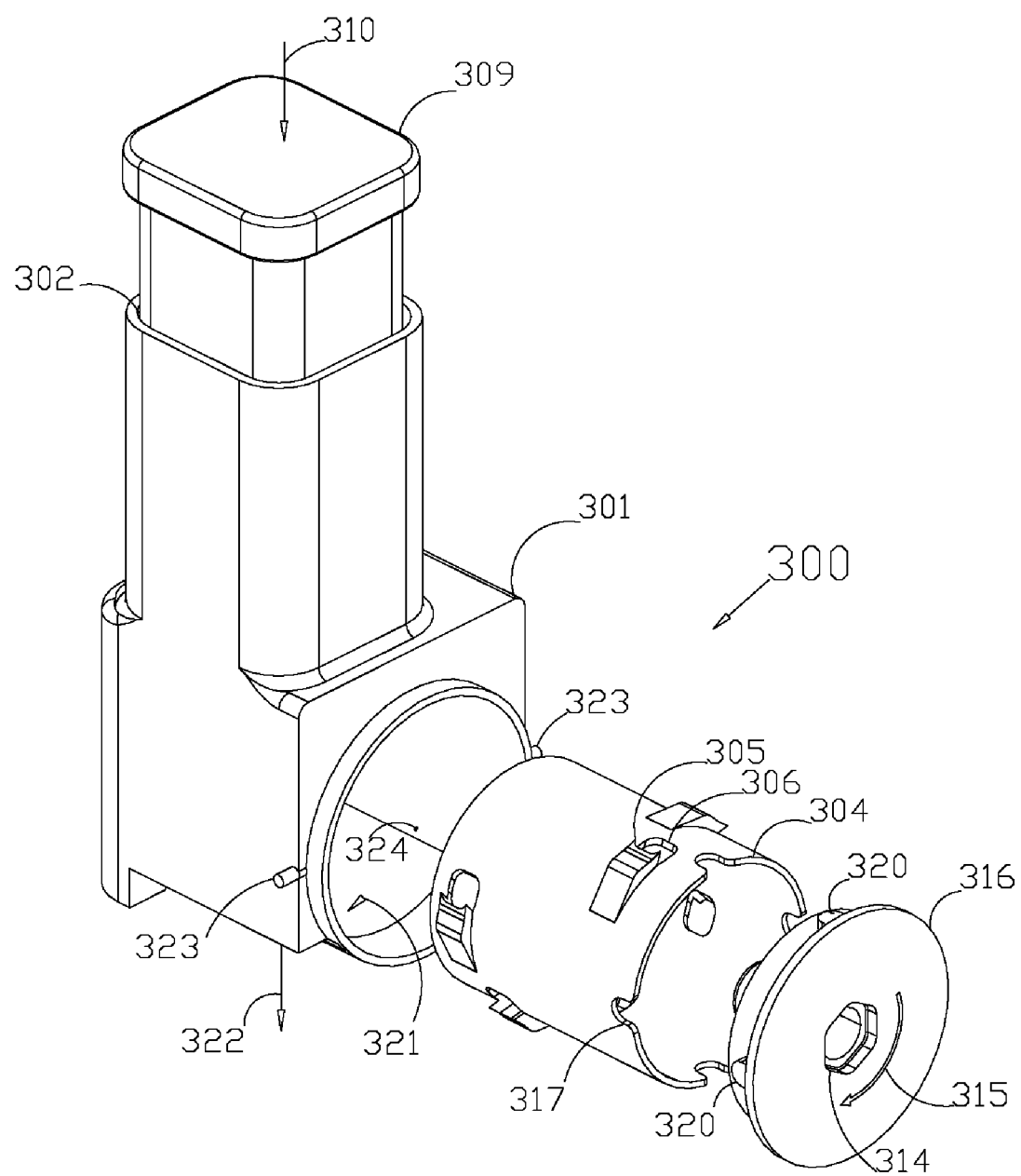
FIG. 9 is a perspective-exploded view of the milling apparatus for milling bone from FIG. 7.

FIG. 9 is another perspective-exploded view of the milling apparatus 300. As shown, the apparatus 300 includes a housing 324 for confining the milled material; and a discharge opening 321 for collecting the milled material that may have escaped the hollow rasp 304. A catch container 406 provided for catching and containing the milled particulates is shown in FIG. 10.

Figure 10:
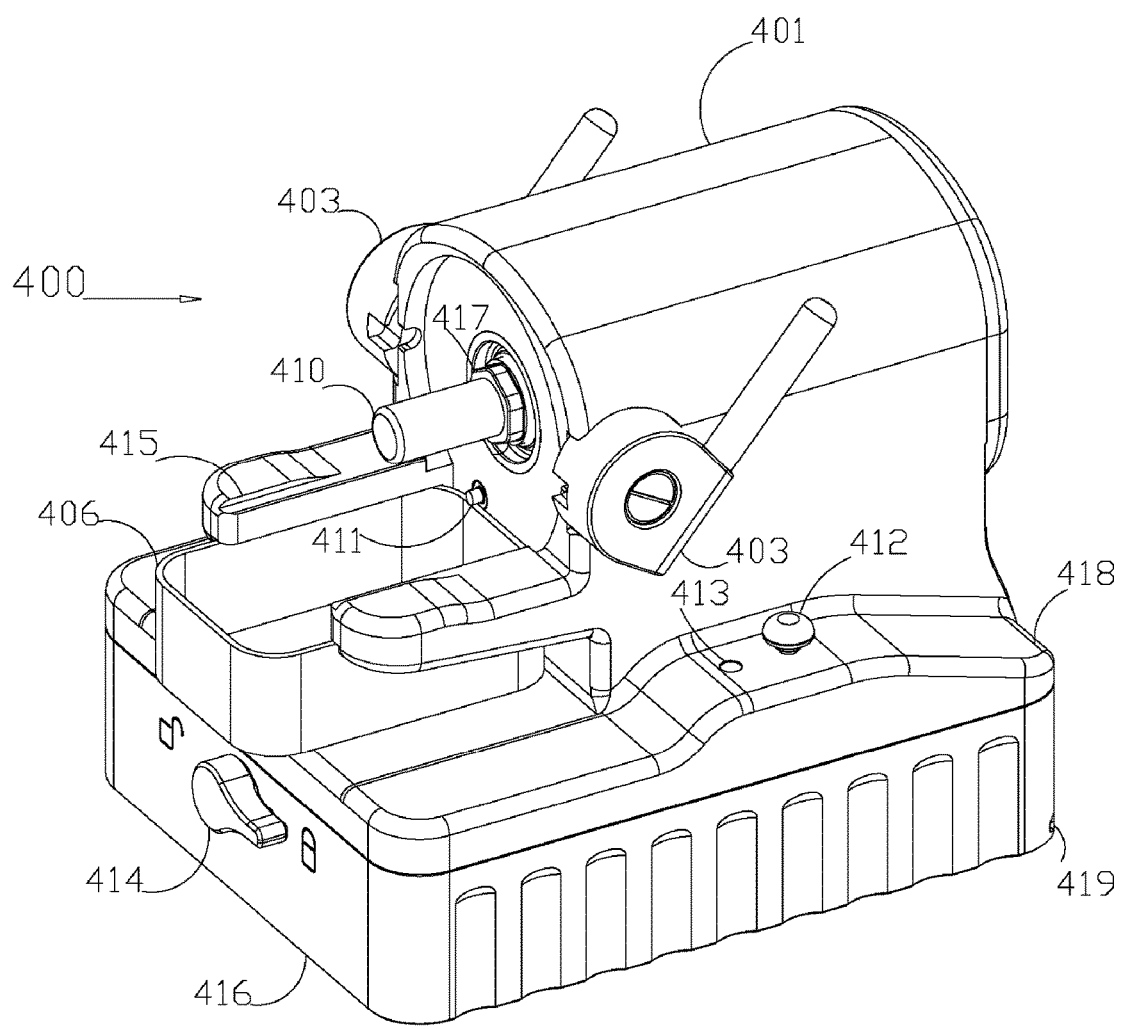
FIG. 10 is a perspective view of a driving power module for milling material.

Two pins 323 provided for attaching the milling apparatus to the driving power-module 400 shown in FIG. 10.

FIG. 10 is a perspective view of a driving power-module 400 that may receive the milling apparatus 300 for milling material. As depicted, a sealed (detail not shown) driving power-module 400 may be autoclavable and battery powered.

The power-module 400 comprises a motor 401, a hollow base 416 for housing a battery-power-pack (detail not shown), shaft 410 with a coupling 417 to mate with the coupling 314 of the lid 316 shown in FIG. 9.

The battery-power-pack (not shown) may include rechargeable batteries, electronic circuit boards for controlling the operation of the mill as wells as the safety features of the mill; and control charging of the batteries, individually.

The base 416 and the motor frame 418 attach to each other with the hinge 419 forming a clamshell configuration (detail not shown). The clamshell configuration may facilitate insertion or removal of the battery-power-pack module.

The motor 401 may be a high torque brushless DC motor. This class of motors driven by electronic circuitry allows controlling the RPM, torque, angular acceleration and deceleration and direction of the motor rotation. For example, in a case of a jam the electronic controlling circuitry of the motor may allow the motor free itself by automatic reverse/forward rotations.

The use of batteries as a power source may eliminate: a) the need for power cords in the crowded hospital operating rooms, b) transportability between the operating rooms eliminating the need for corded power consoles for each operating room.

A pair of cams 403 provided for interfacing with the pins 323 shown in FIG. 9 for locking the apparatus 300 in position as an attachment (detail not shown). Front knob 414 attached to a cam inside the base 416 may lock the base 416 to the motor frame 418 (details not shown). The power-module 400 may include an interlocking safety switch 411, an on-off switch 412, and a light indicator 413. The interlocking safety switch 411 may allow the motor 401 to operate only when the frame 301 attached and secured to the power-driving module 400. The light indicator 413 indicates the status of the operation. For example, a green light indicates readiness for safe operation of the power module 400. For safety, an orange light indicates full electric power applied and it is unsafe to remove the frame 301.

The cams 403 shown in FIG. 10 are in "open" position ready to accept the apparatus 300 as attachment for milling material.

Figure 11:
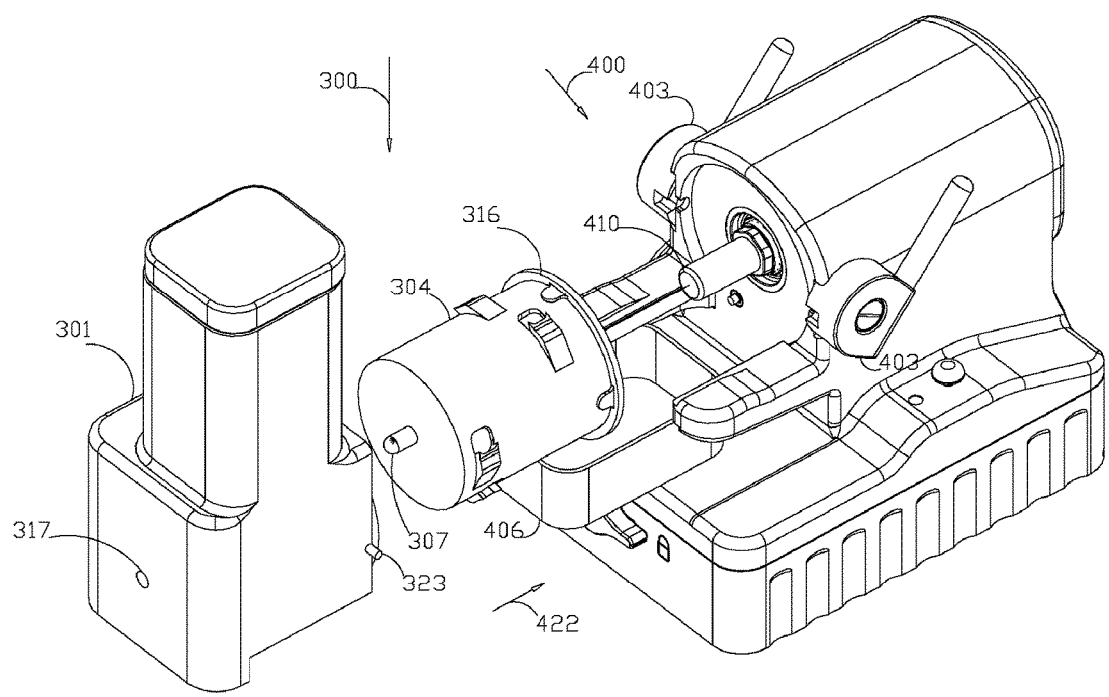
FIG. 11 is a perspective view of the power-driving module from FIG. 10 with milling apparatus.

FIG. 11 is a perspective-exploded view of the power-module 400 and a perspective-exploded view of an embodiment of the milling apparatus 300 in line for attachment.

The preassembled rasp 304 may move in the direction 422 to slide ably mount on the driving shaft 410 to interface with the coupling 417 shown in FIG. 10. Subsequently, the frame 301 may move in the direction 422 to interface with the power-module 400. With the pins 323 inside the cams 403, the cams may manually rotate counterclockwise to pull and secure the frame 301 to the power-module 400.

Figure 12:
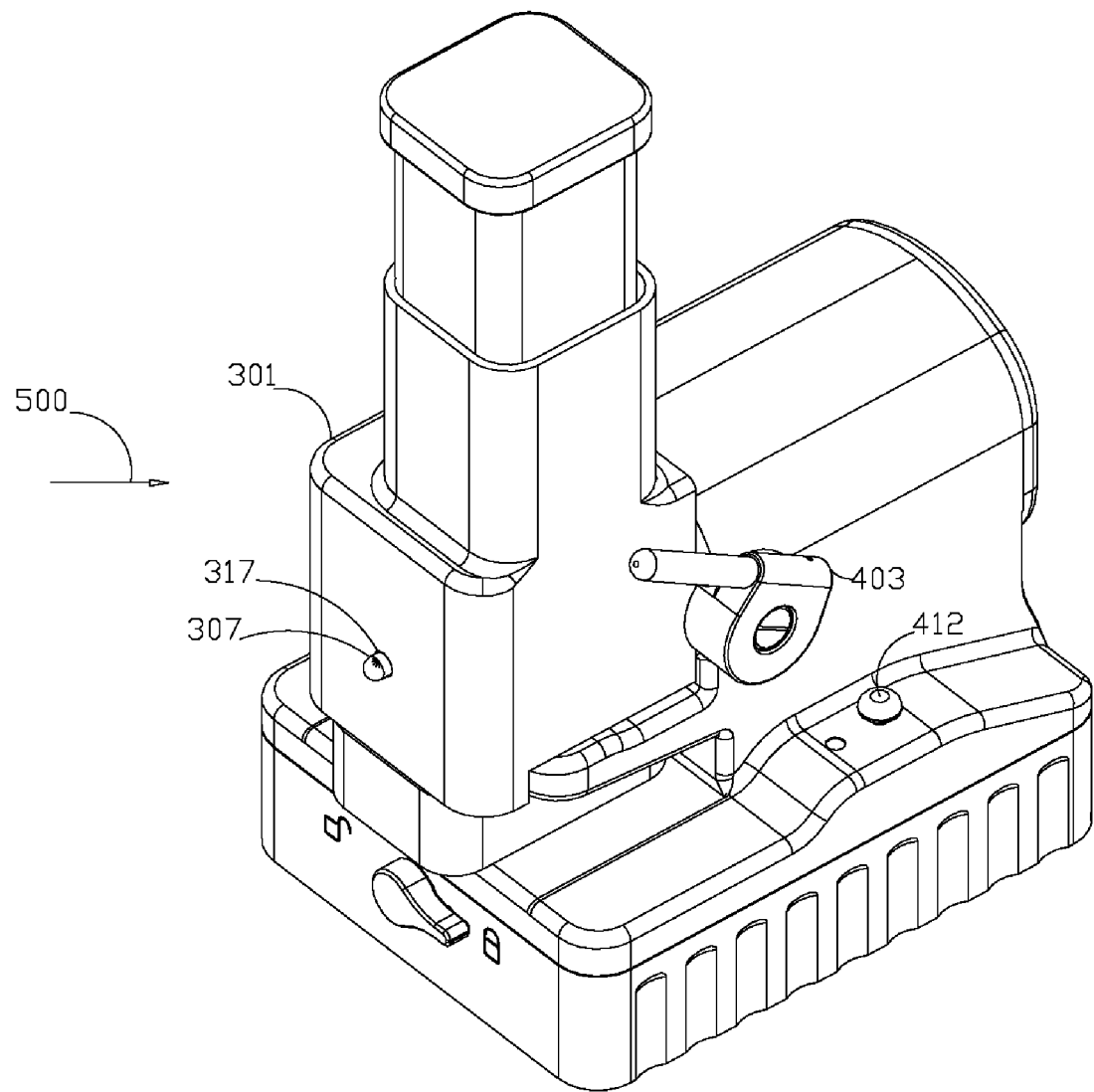
FIG. 12 is a perspective view of an assembled powered milling apparatus.

FIG. 12 is a perspective view of the powered milling apparatus 500 comprising the milling apparatus 300 and the power-module 400 in ready configuration for milling material 303 (see FIG. 7). The milling process may start by pressing the on/off switch 412.

Figure 13:
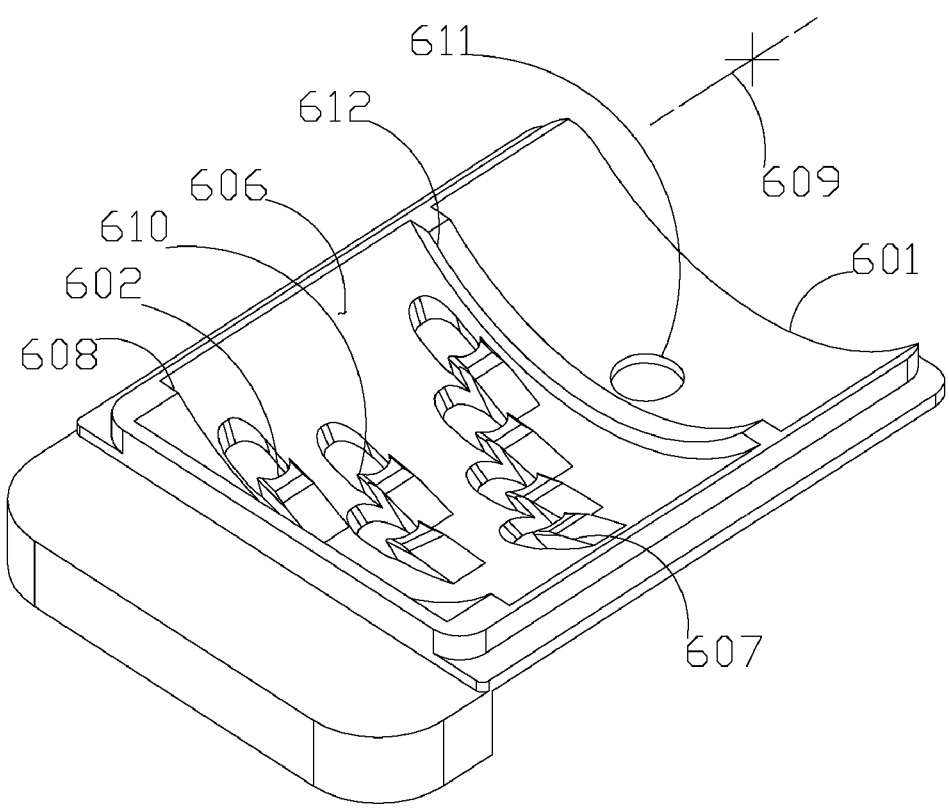
FIG. 13 is a perspective view of a radial rasp for milling bone.
Figure 14:
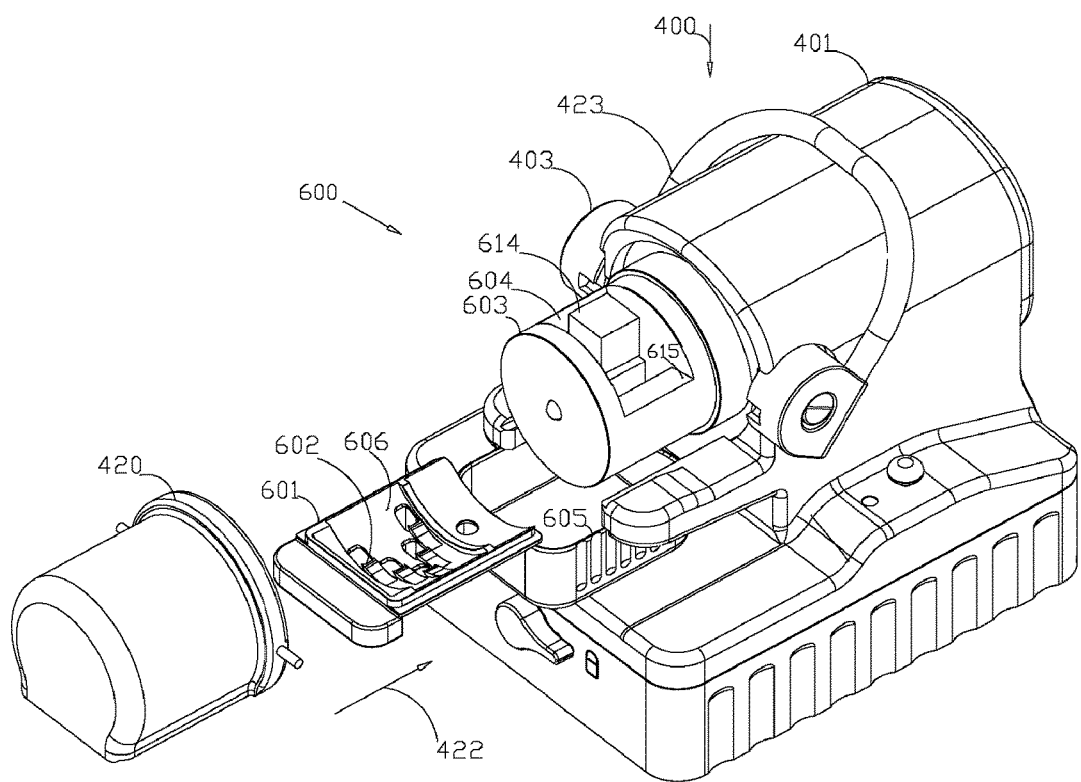
FIG. 14 is a perspective-exploded view of a milling apparatus including the radial rasp from FIG. 13.

FIG. 13 is a perspective view of a radial rasp 601 with radial axis 609 designed to operate in conjunction with the rotor 603 shown in FIG. 14. The radial rasp 601 comprises a radial surface 606 that may extend between the barriers 608 and 612 and may include seven bone-nibbling teeth 607.

The barriers 608 and 612 situated directly beneath the cavity 604 of the rotor 603 may confine the milled particles during milling the material 614 shown in FIG. 14.

The tooth 607 may vary in numbers and sizes (not shown) and may be of the type shown in FIG. 5. In this particular example, the sharp points 610 of the teeth slightly rounded for increased durability.

The opening 611 may provide for holding the rasp 601 during the manufacturing processes.

FIG. 14 is a perspective-exploded view of a milling apparatus 600. The milling apparatus 600 includes a detachable rotor 603; a detachable catch container 605; the rasp 601 having five nibbling teeth; and a safety cap 620 shown in line for attaching to the power-module 400 for milling material 614.

The safety cap 420 confines the material 614 when the rotor 603 rotates.

The rotor 603 comprises a cavity 604 for receiving and containing material 614, a push surface 615 for pushing and sweeping the material 614 over the surface 606 of the rasp 601 when the rotor 603 rotates. The cavity 604 may extend throughout the body of the rotor 603 for receiving maximum amount of material per loading cycle. That is the cavity may not have a bottom surface; the material 614 may rests on the rasp 601, which may provide the bottom.

The advantage of a bottomless cavity is: a) allows accepting more than twice the amount of bone as compared with the double cavity rotor; b) it approximately doubles the rate of milling bone when the cavity filled to its capacity. For example, a two inches diameter rotor with double cavity, disposed on each side of the rotor, allows four cc of bone per filling cycle; the same rotor with single bottomless cavity allows 12 cc of bone per filling cycle, for milling; which may reduce the milling time in the operating room environment.

In practice, a two inches diameter rotor interfacing with a rasp having seven 4 mm wide teeth having side cutters and 5 degrees of negative relief-angle, may produce bone morsels of approximately 4 mm wide and 8 mm long, on the average. The rotor rotating at 2700 RPM may mill cortico-cancellous bone up to two cubic centimeters per second for bone grafting.

The catch container 605 slide ably disposed directly under rotor 603 for catching the milled particulates.

Figure 15:
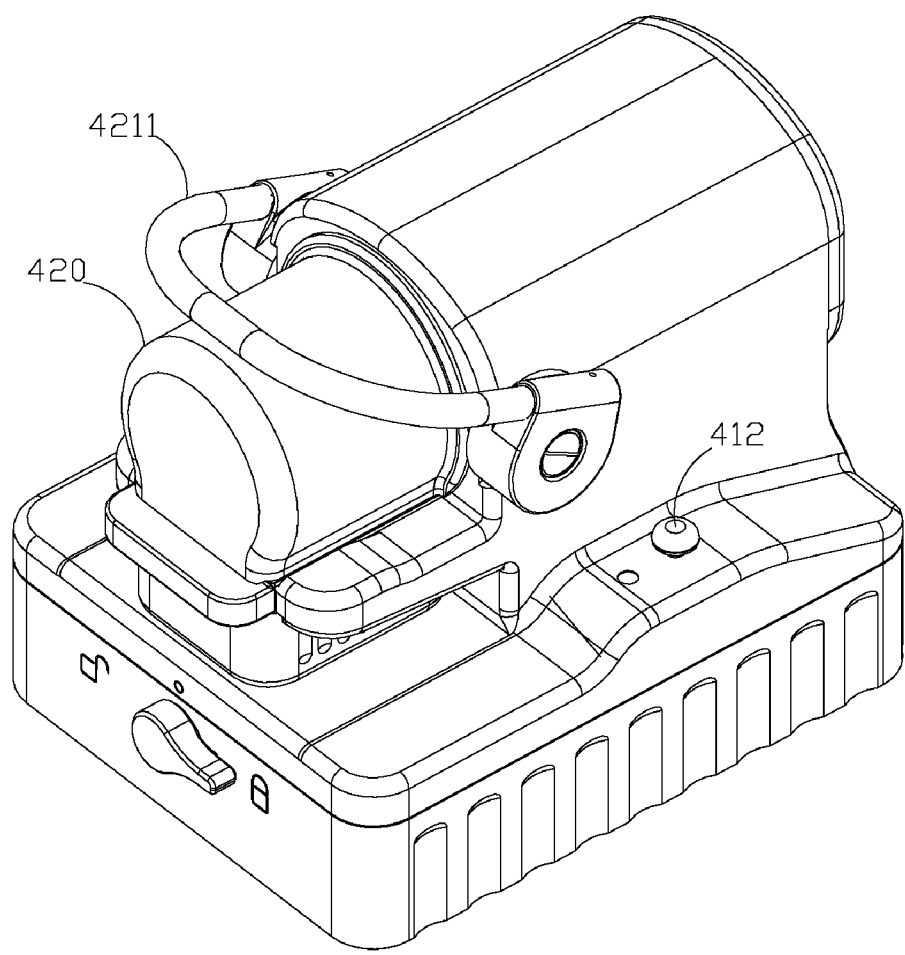
FIG. 15 is perspective view of assembled milling apparatus from FIG. 14.

FIG. 15 is a perspective view of an embodiment of the assembled milling apparatus 600, which may mill cortical, cancellous, or corticocancellous bone having predetermined particle-size distribution profile for bone grafting procedures.

The described aspects may be implemented in other specific forms without departing from its spirit or essential characteristics. The described aspects are to be considered in all respects only as illustrative and not restrictive. The scope is, therefore, indicated by the appended claims rather than by the foregoing description. All changes which come within the meaning and range of equivalency of the claims are to be embraced within their scope.

What is claimed is:

1. An apparatus for milling material, comprising:
   a base surface;
   a cutting tooth attached to and raised from the base surface further comprising:
      a cutting edge, a relief surface, and a rake face,
      the relief surface having a negative relief angle with respect to the base surface,
      the rake face positively inclined with respect to the base surface and including side cutting edges with cutting angles less than ninety degrees;
   an aperture in the base surface having a predetermined size disposed adjacent to the rake face permitting material of less than the predetermined size to pass through the aperture; and
   a push surface; and
   wherein the base surface and the push surface are operable to move in linear opposite directions relative to each other to move the material and to cut the material with the cutting edge and the side cutting edges.

2. The apparatus of claim 1, wherein a portion of the relief surface rises above the cutting edge relative to the base surface.

3. The apparatus of claim 1, wherein the base surface further comprises:
- a second cutting tooth comprising: a second relief surface having a negative relief angle with respect to the base surface, a second rake face positively inclined with respect to the base surface, the second rake face having side cutting edges with cutting angles less than ninety degrees; and
- a second aperture disposed adjacent to the second rake face.

4. The apparatus of claim 3, wherein the cutting tooth and the second cutting tooth are laterally offset from each other on the base surface.

5. The apparatus of claim 3, wherein the cutting tooth and the second cutting tooth are longitudinally offset from each other on the base surface.

6. The apparatus of claim 1, further comprising a driving power module configured to power centrifugal force operative to push the material on the base surface for milling; and
- wherein the base surface and the push surface move rotationally relative to each other to interoperatively cut the material during the relative movement of the base surface and the push surface.

7. The apparatus of claim 1, further comprising a drive mechanism for moving the base surface and the push surface relative to each other.

8. An apparatus for milling material to a predetermined particle size, comprising:
- a base surface;
- a cutting tooth attached to and raised from the base surface further comprising:
  - a cutting edge, a relief surface, and a rake face,
  - the relief surface having a negative relief angle with respect to the base surface,
  - the rake face positively inclined with respect to the base surface; and
- an aperture in the base surface having a predetermined size disposed adjacent the rake face permitting material of less than the predetermined size to pass through the aperture; and
- a push surface; and
- wherein the base surface and the push surface are operable to move in linear opposite directions relative to each other to move the material and to cut the material with the cutting edge when placed on the base surface during the movement of the base surface relative to the push surface.

9. The apparatus of claim 8, wherein a portion of the relief surface rises above the cutting edge relative to the base surface.

10. The apparatus of claim 8, further comprising a driving power module configured to power centrifugal force operative to push the material on the base surface for milling; and
- wherein the base surface and the push surface move relative to each other to interoperatively cut the material during the relative movement of the base surface and the push surface.

* * * * *